United States Patent
Böhme et al.

(10) Patent No.: US 12,324,771 B2
(45) Date of Patent: Jun. 10, 2025

(54) POSITIONING DEVICE

(71) Applicant: Carl Zeiss Meditec AG, Jena (DE)

(72) Inventors: Beate Böhme, Großpürschütz (DE); Gregor Stobrawa, Jena (DE); Karsten Festag, Jena (DE); Marco Lehnort, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 448 days.

(21) Appl. No.: 17/637,796

(22) PCT Filed: Sep. 8, 2020

(86) PCT No.: PCT/EP2020/075035
§ 371 (c)(1),
(2) Date: Feb. 23, 2022

(87) PCT Pub. No.: WO2021/048100
PCT Pub. Date: Mar. 18, 2021

(65) Prior Publication Data
US 2022/0280338 A1    Sep. 8, 2022

(30) Foreign Application Priority Data
Sep. 10, 2019 (DE) .................. 10 2019 213 698.2
Dec. 6, 2019 (DE) .................. 10 2019 219 122.3

(51) Int. Cl.
*A61F 9/008* (2006.01)
*A61B 3/14* (2006.01)

(52) U.S. Cl.
CPC ........... *A61F 9/008* (2013.01); *A61B 3/14* (2013.01); *A61F 2009/00844* (2013.01)

(58) Field of Classification Search
CPC ... A61F 9/008; A61F 2009/00844; A61B 3/14
See application file for complete search history.

(56) References Cited

U.S. PATENT DOCUMENTS 6,175,642 B1    1/2001   Gobbi et al.
6,322,216 B1 *  11/2001  Yee .................. A61F 9/00804
                                                 606/5
(Continued)

FOREIGN PATENT DOCUMENTS

DE    102005032946 A1    2/2006
DE    102005013949 A1    9/2006
(Continued)

OTHER PUBLICATIONS

International Search Report for PCT/EP2020/075035, mailed Nov. 3, 2020, 4 pages.
(Continued)

*Primary Examiner* — Lynsey C Eiseman
*Assistant Examiner* — Skylar Lindsey Christianson
(74) *Attorney, Agent, or Firm* — DeWitt LLP

(57) ABSTRACT

An ophthalmological laser therapy positioning device which facilitates accurate positioning of the laser therapy system vis-à-vis the patient's eye. The positioning device includes a first and a second recording unit, which provide recording data from different recording directions, a displacement unit that displaces the relative position of the eye vis-à-vis an optical opening of the laser therapy system on the basis of control commands, and a control unit that generates control commands on the basis of the recording data. The positioning device furthermore may include a display unit for displaying the recording data and an input unit for inputting input data, the control unit in this case generates control commands on the basis of the recording data and/or on the basis of the input data and to provide the control commands to the displacement unit. Corresponding positioning methods are also included.

15 Claims, 3 Drawing Sheets

(56) References Cited

U.S. PATENT DOCUMENTS

| | | | |
|---|---|---|---|
| 10,123,696 B2 | 11/2018 | Schuele et al. | |
| 2006/0192921 A1* | 8/2006 | Loesel | A61F 9/008 351/219 |
| 2007/0055222 A1* | 3/2007 | Hohla | A61F 9/00806 606/5 |
| 2007/0299429 A1 | 12/2007 | Amano | |
| 2010/0042081 A1 | 2/2010 | Rathjen | |
| 2013/0296834 A1 | 11/2013 | Wellhoefer et al. | |
| 2014/0046308 A1 | 2/2014 | Bischoff et al. | |
| 2015/0272782 A1 | 10/2015 | Schuele et al. | |
| 2017/0205715 A1* | 7/2017 | Huebner | G03F 9/7011 |
| 2017/0347877 A1 | 12/2017 | Frey | |
| 2018/0092705 A1 | 4/2018 | Ootsuki | |
| 2021/0038426 A1 | 2/2021 | Boularot et al. | |

FOREIGN PATENT DOCUMENTS

| | | |
|---|---|---|
| DE | 102006053580 A1 | 9/2007 |
| EP | 1223847 A1 | 7/2002 |
| WO | WO 01/24688 A1 | 4/2001 |
| WO | WO 2010/000279 A1 | 1/2010 |
| WO | WO 2016/058931 | 4/2016 |
| WO | WO 2019/068866 | 4/2019 |

OTHER PUBLICATIONS

English translation of International Search Report for PCT/EP2020/075035, mailed Nov. 3, 2020, 2 pages.

International Preliminary Report on Patentability for PCT/EP2020/075035, mailed Mar. 24, 2022, 11 pages.

\* cited by examiner

POSITIONING DEVICE

RELATED APPLICATIONS

This application is a National Phase entry of PCT Application No. PCT/EP2020/075035 filed Sep. 8, 2020, which application claims the benefit of priority to DE Application No. 10 2019 213 98.2 filed Sep. 10, 2019, and DE Application No. 10 2019 219 122.3, filed Dec. 6, 2019, the entire disclosures of which are incorporated herein by reference.

TECHNICAL FIELD

The present invention relates to a positioning device for an ophthalmological laser therapy system with an optical opening, for positioning an eye vis-à-vis the optical opening. The invention furthermore relates to an ophthalmological laser therapy system. Finally, the invention relates to a method for a positioning device of an ophthalmological laser therapy system with an optical opening, for positioning a patient's eye vis-à-vis the optical opening.

BACKGROUND

Combining a laser therapy apparatus for producing incisions in an ocular tissue or for ablating or coagulating ocular tissue by application of laser radiation with an observation device for controlling and monitoring various work steps during the therapeutic intervention now is conventional in ophthalmological laser therapy.

By way of example, this is very advantageous in laser-assisted eye surgery for correcting a refractive error or for the therapy of other ocular diseases, for example for treating a cataract by cataract surgery. Monitoring the work steps is also required in refractive error corrections such as for example a "SMILE" treatment, that is to say a small incision lenticule extraction, an implantation of a lenticule or in other modifications to the cornea, in order to be able to interrupt the application of the incisions in the cornea when necessary. After the application of the incisions in the ocular tissue, the lenticule is removed (or modified) or an implant is introduced under observation—for example by application of a surgical microscope (also referred to as an OPMI).

An important work step in the preparation of ophthalmological laser therapy (particularly when using fs lasers) is an alignment of the laser therapy system vis-à-vis the eye, or even a fixation of the eye. This is frequently implemented using a contact element (e.g., a contact glass), which the operator (surgeon, assistant or generally a user) of the ophthalmological laser therapy system must bring into contact with the patient's eye. Subsequently, the eye is immobilized vis-à-vis the laser therapy system. Appliance parameters are optionally to be adjusted, depending on the relative position of the immobilized eye in relation to the laser therapy system. Only then can the user start the therapy process, the course of which said user must monitor as a rule.

DE 102005013949 describes an ophthalmological laser therapy system for treating the human eye, comprising a beam source and apparatuses for scanning the focused laser beam on the eye in three dimensions (x, y, z). In this case, a contact glass is situated on the cornea of the eye and bears against the cornea of the eye. A beam splitter is arranged in the beam path of the laser therapy system and used to at least partially deflect beams emanating from the eye in the direction of a tube with an eyepiece (for direct observation by the operator) or an objective lens with a camera. This facilitates a co-observation of the cornea while light from an fs laser impinges the eye (therapy). Although the described arrangement allows monitoring of the therapy, controlling the positioning of the laser therapy system vis-à-vis the patient's eye and the docking of the eye on the contact glass is only provided by this co-observation arranged coaxially with respect to the therapy beam path.

WO 2016/058931 describes an ophthalmological laser therapy system comprising a laser system (for therapy) and a surgical microscope (for examination), which can be connected to one another. The arrangement disclosed here also allows the therapy to be monitored while there is no provision for controlling the positioning of the eye.

Further laser therapy systems, as described in DE 102005032946A1 and U.S. Ser. No. 10/123,696B2, also merely allow an observation (and monitoring) of the eye using a beam path running coaxially with respect to the therapy beam path. Thus, in DE 102005032946A1, the same image is coupled into both parts of a binocular beam path of the surgical microscope with the observation direction running coaxially with respect to the therapy beam path. WO 2019/068866 discloses a camera system which is directed at the eye at an observation angle in relation to the therapy beam path, and this too can only be used for observation purposes during the therapy (or immediately before the eye bears against the contact element).

None of these systems are suitable for facilitating a positioning of the eye vis-à-vis the ophthalmological laser therapy system.

SUMMARY OF THE INVENTION

Example embodiments of the present invention remove the disadvantages of the prior art and provide a solution for a positioning device for an ophthalmological laser therapy system which facilitates an accurate, fast, user-friendly and intuitive positioning of the laser therapy system vis-à-vis the patient's eye.

A first aspect of the invention relates to a positioning device for an ophthalmological laser therapy system with an optical opening, for positioning an eye vis-à-vis the optical opening.

An ophthalmological laser therapy system is designed to carry out an ophthalmological therapy when used by a user (operating physician, surgeon, operator). Here, an ophthalmological therapy should be understood to mean any therapy in which ocular tissue is modified. In particular, the ophthalmological therapy contains corresponding laser-surgical interventions, in which ocular tissue is "cut" (for example, a lenticule or flap) by photodisruption by use of a laser, for example a pulsed laser such as a femtosecond or excimer laser for example, in which a region of an ocular tissue is ablated by an ablation effect or in which ocular tissue is "adhesively bonded" to itself by a coagulation effect, or in which the refractive index of the material, that is to say of an ocular tissue or else an implant, is modified by the laser radiation.

By way of example, the light from a laser source can emerge from the laser therapy system via the optical opening of the ophthalmological laser therapy system and—if the eye is positioned at a target position or near the target position—penetrate the patient's eye in order to carry out the planned therapy there. Thus, the optical opening may be an exit opening for therapy radiation (the laser exit opening). Light reflected or scattered by the eye can also enter the laser therapy system via the optical opening of the ophthalmological laser therapy system and—in the case of suitable positioning in or near the target position—thus facilitate an examination of the eye (or an observation of the eye for "manual" surgical steps such as the removal of a lenticule). Thus, the optical opening may be an entrance opening for examination radiation.

The optical opening may be formed as a contact element or contact glass. The optical opening may be the final lens element of a surgical microscope.

According to the invention, the positioning device comprises a first recording unit (also referred to as observation unit) designed to provide first recording data (also referred to as observation data) of the eye from a first recording direction (also referred to as observation angles). Furthermore, the positioning device comprises a second recording unit designed to provide second recording data of the eye from a second recording direction. In this case, the second recording direction differs from the first recording direction. The recording direction of a recording unit should be understood to mean a vector which points from the recording unit in the direction from which recording data can be recorded; it points in the "viewing direction" of the recording unit. The target position of the eye is for example in the viewing direction of the recording unit. An angle between the two recording directions is preferably not 180°. The two recording units, which may be designed, for example, as cameras with two-dimensional sensors and with camera optical units (also referred to as recording optical unit or observation optical units), therefore allow the eye to be observed from two different angles.

A recording unit is preferably small, that is to say the visible optical unit diameter of the recording optical unit is less than 10 mm, for example less than 5 mm, and/or the f-number is greater than 2. Furthermore, the sensor (e.g., CCD, CMOS) of the recording unit is for example smaller than 10 mm×8 mm, the sensor pixels are smaller than 3 µm×3 µm and/or the sensor has at least 1900×2500 pixels. The recording unit preferably has a volume of less than 3 cm×3 cm×3 cm.

Furthermore, the positioning device comprises a displacement unit designed to displace the relative position of the eye vis-à-vis the optical opening on the basis of control commands. Here, the displacement unit may be for example designed to displace the optical opening. Alternatively or in addition, the displacement unit may be designed to displace the eye—for example by displacing a patient couch on which the patient is situated. Preferably, a displacement in all three spatial directions is facilitated. Direction and speed of the displacement are controlled by way of control commands. According to the invention, these are provided by a control unit which is likewise part of the positioning device. The control unit can be a computer comprising a processor and a memory. The control unit is designed to generate the control commands on the basis of the recording data. This can be implemented by combining the recording data by calculation (for example in a computing unit which is part of the control unit). In the process, a position of the eye vis-à-vis the ophthalmological laser therapy system and its optical opening can be calculated by way of two-dimensional recording data from the two different recording directions. Preferably, the relative positions of the recording units and the recording directions thereof (and/or for example a magnification or a focal position as well) are considered when calculating the three-dimensional position of the eye. Additionally, the relative positions of the optical opening vis-à-vis the recording units may be considered when calculating the relative position between the optical opening and the eye. The required control commands for the displacement unit may be derived from the ascertained position of the eye vis-à-vis the optical opening.

The positioning device according to the invention facilitates automatic positioning of the eye vis-à-vis the optical opening of the ophthalmological laser therapy system.

The positioning may also comprise the docking on a contact glass. The result of the positioning may be verified by the operator; in this case, the verification need not be implemented by way of the positioning device. Following the verification, the operator may repeat the positioning or start the therapy of the eye.

The recording units are preferably fixed permanently to the ophthalmological laser therapy system. If the ophthalmological laser therapy system has a stationary appliance base and an appliance head movable (for example laterally in the x- and y-directions and/or in the height z) in relation thereto, a recording unit is preferably fastened to the appliance head. If a laser pivot arm (for providing therapy radiation) and an examination pivot arm (for examining examination radiation) are fastened to the appliance head and said arms have the optical opening which can be moved vis-à-vis the appliance base (preferably in the z-direction but also in the x- and y-directions), the other recording unit is preferably fastened to one of the pivot arms—particularly preferably to the laser pivot arm. Positioning on the laser pivot arm is therefore preferred since precise positioning of the eye vis-à-vis the optical opening is significantly more critical for the therapy than for an examination. Furthermore, the recording optical unit is preferably arranged close to the optical opening.

An alternative positioning device for an ophthalmological laser therapy system with an optical opening, for positioning an eye vis-à-vis the optical opening, comprises a first recording unit designed to provide first recording data of the eye from a first recording direction. Furthermore, it comprises a second recording unit designed to provide second recording data of the eye from a second recording direction, the second recording direction differing from the first recording direction. Moreover, the positioning device comprises a displacement unit designed to displace the relative position of the eye vis-à-vis the optical opening on the basis of control commands. In this case, the descriptions of the recording units and the displacement unit provided above also apply to this alternative positioning device.

Additionally, the positioning device comprises a display unit for displaying the first and second recording data of the eye. To this end, the recording data may initially be converted into display data. On account of the different recording directions of the recording units, the operator is put in a position to recognize the three-dimensional position of the eye on the display unit provided the eye is situated in the image fields (frequently also referred to as object fields) of the recording units.

Preferably, the display unit is close to the location adopted by the operator during the therapy or during the preparation thereof (e.g., when docking the eye on the contact glass). For example, the display unit is in the line of sight of and at a comfortable viewing distance from the operator. By way of example, the display unit may be connected to the laser pivot arm or to the examination pivot arm. Furthermore, additional information or menus for controlling the laser therapy system may be displayed to the operator on this display unit.

Furthermore, the positioning device comprises an input unit which facilitates an input of input data by the operator. By way of example, the input unit may be one or more buttons, a keyboard, a rotary controller and/or a slide controller. The input unit may also be integrated in the display unit as a touch screen. A joystick which may additionally have one or more buttons is an option.

Moreover, the positioning device comprises a control unit. The latter is designed to provide control commands on the basis of the recording data (in accordance with the descriptions of the control unit provided above). Additionally or as an alternative, it is designed to generate control commands on the basis of the input data from the input unit. Thus, the input data can be converted by the control unit into the control commands for the displacement unit; this is for example implemented in a computing unit which may be part of the control unit. The generated control commands may be provided to the displacement unit. The control unit can be a computer comprising a processor and a memory.

By way of such a positioning device, the operator is put in a position to recognize the position of the eye on the display unit, manually control the displacement unit via the input unit and consequently align the optical opening of the ophthalmological laser therapy system vis-à-vis the eye. Additionally or as an alternative, positioning may be carried out automatically. The recording data displayed on the display unit may serve the operator when monitoring the positioning procedure and/or when verifying the result of the positioning.

In an example configuration of the positioning device, the first recording unit comprises a first recording optical unit and the second recording unit comprises a second recording optical unit. In this case, at least one recording optical unit has on the object side, that is to say at the eye, a numerical aperture of less than 0.25, for example less than 0.1, in another example less than 0.05. In this way, the eye is for example already imaged in focus or sufficiently in focus before it reaches its target position (for example before the cornea bears against the contact element)—for example already at a distance of 100 mm to 200 mm from the contact element—and so the operator can start with positioning and/or the control unit can generate control commands for the displacement unit.

The ophthalmological laser therapy system typically has an optical unit. According to a configuration of the positioning device for such a therapy system, the first recording unit comprises a first recording optical unit. In this case, a part of the optical unit of the ophthalmological laser therapy system and a part of the first recording optical unit are identical.

For example, a part of a laser optical unit of the laser pivot arm or a part of an examination optical unit of the examination pivot arm is identical to a part of the first recording optical unit. That is to say, a part of the optical unit of the laser pivot arm for guiding the laser light from the laser source to the eye (or a part of the optical unit of the examination pivot arm) is also used by the recording optical unit of a first recording unit for observing the eye. The jointly used optical unit may comprise the optical opening. A beam path of the first recording unit may be formed at an angle of less than 20° in relation to a beam path in the laser pivot arm or in the examination pivot arm. The beam paths may also be formed coaxially.

To achieve a compact structure, the first recording optical unit advantageously has a high f-number and small diameters on the sensor side.

The imaging scale of the first recording optical unit is for example chosen such that an entire treatment area or examination area of the eye (e.g., a diameter of approximately 10 mm in the correctly positioned or docked state) is imaged in focus. To this end, the recording optical unit can be designed such that its focus coincides with the focus of the laser optical unit or examination optical unit, for example on or just behind (that is to say in the eye) of a final surface of the contact element.

A recording unit with a jointly used optical unit permits a "transmitted view" of the eye. A transmitted view is particularly suitable for facilitating a centration of the eye vis-à-vis the optical opening. At the same time, it allows the progress of the treatment to be observed during surgery.

Typically, the beam path of the recording unit is separated from the beam path of the laser optical unit or examination optical unit (or brought together therewith) by way of a beam splitter in the case of a jointly used optical unit. The beam splitter may be embodied as a beam splitter cube. If the first recording optical unit additionally has a small numerical aperture on the object side (as described above), the beam splitter may for example be formed as a plane plate which is oriented at an angle in the beam path. What is advantageous here in turn is that the beam path of the recording unit is guided in transmission and the beam path of the laser optical unit or examination optical unit in reflection. The high quality of the image representation by the recording unit is maintained as a result of the small numerical aperture on the side of the eye. Using a plane plate saves costs and, especially, weight.

In an example development of the described configuration, the first recording optical unit is designed such that an image field of an observed area is imaged with a constant image field size or a larger image field size with increasing distance from the first recording optical unit.

A constant image field size (frequently also referred to as object field size) can be obtained by virtue of the recording optical unit having a telecentric design on the object side. This means that an observed area with a size of 10 mm diameter is imaged, for example even for a distance of 100 mm to 200 mm between the optical opening and the contact element.

A larger image field size of the observed area can be obtained by a deviation from the object-side telecentricity of the recording optical unit such that the observed area becomes larger with increasing distance and a larger part of the eye or patient's head becomes visible. An increase is advantageous as it facilitates a larger "capture region"; that is to say the eye is already in the image field of the recording unit even in the case of relatively large deviations from its target position vis-à-vis the optical opening.

The described embodiments of the first recording unit, which provides a transmitted view, are also suitable for observing the eye during laser therapy and consequently monitoring the therapy. Therefore, its use is not limited to a positioning process.

Even a recording unit not providing a "transmitted view" may comprise a recording optical unit designed such that an image field of an observed area is imaged with a constant image field size or a larger image field size with increasing distance from the first recording optical unit. This also facilitates an improvement in the "capture region".

According to a configuration of the positioning device, a recording unit has an image field size of at least 30 mm×30 mm, for example at least 40 mm×40 mm, in another example at least 50 mm×50 mm in a focal plane; that is to say an object of this size located in the focal plane is imaged in focus on the sensor of the recording unit. The focal plane of the recording unit (or its recording optical unit) is for example located at (or near) the target position of the eye. Even if the treatment area or examination area only has a diameter of approximately 10 mm, the greater image field size according to the invention facilitates a recognition of the eye even if it is not yet in its target position since the image field also comprises structures of the patient's head that surround the eye. For example, the "capture region" can be further improved in this way—beyond the solution described above.

In a configuration of the positioning device, the first recording direction and the second recording direction include an angle of 90°±30° with respect to one another, for example 90°±10°, in another example 90°±5°.

Expressed differently, recording data of the eye are provided by two recording units from two spatial directions which include an angle of approximately 90° with respect to one another. This angle allows the position of the eye to be determined more accurately than what would be possible using a small angle.

For example, at least one recording direction corresponds to a movement direction of the displacement unit. Furthermore, a recording direction substantially parallel to the direction with which laser light is guided to the eye from the optical unit of the laser pivot arm is preferred. For example, the recording unit with this recording direction comprises a recording optical unit, a part of the optical unit of the ophthalmological laser therapy system and a part of the first recording optical unit being identical.

By way of example, the first recording direction can be a transmitted view which facilitates a centration of the eye with respect to the optical opening particularly well. The second recording direction can be a side view of the eye. The latter facilitates a convergence between eye and optical opening particularly well. In an example embodiment, the side view has a large image field size in the focal plane (as described above) in order thus also to be able to capture the parts of the patient's head that surround the eye (e.g., eye socket, forehead and nose). While the transmitted view facilitates precise centration, the side view facilitates a precise (axial) approach of the eye by the optical opening (especially if a large capture region is realized).

According to a further configuration, the positioning device comprises a third recording unit designed to provide third recording data from a third recording direction, the third recording direction differing from the first and the second recording direction.

To this end, the three recording units (or their recording angles vis-à-vis the target position of the eye) may form an orthogonal coordinate system. However, they may also have smaller (or larger) angles with respect to one another. By way of example, it is sufficient for the third recording unit to be arranged outside of the plane spanned by the two other recording units and the target position of the patient's eye in order, in the control unit (or a computing unit optionally contained therein), to improve the calculation of a position of the eye vis-à-vis the optical opening. The third recording data may likewise be displayed by the optionally present display unit.

Preferably, the third recording unit also has a large image field size in a focal plane. If two recording units are configured with large image field sizes, the "capture region" for a positioning is further improved.

In an example variant of the positioning device, the third recording direction and the first recording direction include an angle of more than 10° and less than 90° with respect to one another, for example 20° and 70°, in another example between 30° and 60°.

The angles according to the invention firstly ensure that the recording unit can "see" the eye: Since the patient's eye is in the eye socket, it cannot be seen from all directions. In addition to a transmitted view (e.g., realized by way of the first recording unit) and a side view (e.g., by way of the second recording unit), a third recording direction perpendicular to the two recording directions does not provide a clear view of the eye, and so the specified angle should be less than 90°. Then again, the angles according to the invention bring about an improvement in the calculation of the relative position between eye and optical opening since the third recording direction offers a new, independent "viewing direction" with respect to the eye vis-à-vis the first recording direction.

Since a direct view of the operator on the patient's eye may be concealed by parts of the ophthalmological laser therapy system if the optical opening and the eye are positioned (rather) well with respect to one another for a therapy, the third recording unit is for example positioned on the laser therapy system so that the recording data are recorded at an observation angle (that is to say with a recording direction) that corresponds to the direct, unobstructed view of the operator on the eye. This is ensured by way of the aforementioned angle ranges. Consequently, the third recording unit facilitates what is known as a "plan view" of the eye. Optionally, these recording data are also displayed on the optionally present display unit.

For example, the third recording direction and the second recording direction include an angle of 90°±30° with respect to one another, for example 90°±10°, in another example 90°±5°.

In a further configuration, the positioning device comprises a fourth recording unit designed to provide fourth recording data from a fourth recording direction. In this case, the fourth recording direction differs from the first, second and third recording directions. In particular, the fourth recording direction and the first, second or third recording direction include an angle of 180°±30°, for example 180°±10°, in another example 180°±5° with respect to one another.

If for example the second recording unit facilitates a side view of a first (e.g., right) eye, the fourth recording unit may facilitate for example the side view of the second (e.g., left) eye without for example the patient's nose or other parts of the head restricting a lateral view of the eye.

If recording data of two or more recording units are displayed, it is for example advantageous if it is not the entire recording data that are shown but only an image section (a so-called "region of interest", ROI) of the recording data in each case. The ROIs may be chosen—for example by a computing unit—such that the displayed recording data contain the eye. The ROI of the first recording unit which provides a transmitted view for example has a rectangular, square shape (for example with 900×900 pixels) or a circular shape and the ROIs of the second and third recording unit, which offer a side view and a plan view, respectively, have a rectangular shape (for example with 700×450 pixels). These ROIs may be converted into a conventional video format (e.g., in the computing unit) in real time (for example with a latency between image recording and display of less than 0.5 seconds) and may be shown by the display unit. By way of example, the resultant video then has a minimum size of 1600×900 pixels.

In a further configuration of the positioning device, the control unit comprises a computing unit designed to combine recording data from a recording unit with a target mark by calculation to form display data. The control unit can provide the display data.

The target mark may be a marking indicating the target position of the eye vis-à-vis the optical opening (e.g., the contact glass). This marking may be shaped as a line, cross, circle or any other symbol. The marking may also be a (stylized) representation of the contact glass (optionally together with the adjoining optical unit). This target mark may be overlaid on the recording data in the computing unit and jointly converted into display data that are shown on the display unit. The target mark is for example displayed such that it has a good contrast (e.g., in brightness and/or color) vis-à-vis the displayed recording data.

To overlay the target mark on the recording data, the image content of the recording data may be evaluated by the computing unit, for example in order to recognize the eye, parts of the eye such as the iris or the pupil and/or parts of the ophthalmological laser therapy system such as the optical opening (or the contact glass) in the data.

The display of the target mark on the display unit may improve the positioning of the eye vis-à-vis the optical opening since the operator is provided with visual assistance for a manual control of the displacement unit.

The control unit may be designed to calculate displacement data on the basis of the recording data, said displacement data representing a displacement direction or a displacement distance, for example. These displacement data may also be displayed on the display unit, for example as arrows that mark the displacement direction or the displacement distance—for example overlaid on recording data. This can indicate to the user how they should control the displacement unit (by way of the input unit).

In a further configuration, the positioning device comprises an illumination unit designed to impinge the eye with illumination light.

The quality of the recording data may be improved by use of the illumination unit, and so the operator or the control unit can generate control commands for the displacement unit with increased precision.

The illumination unit may guide illumination light via the optical opening (e.g., via the contact glass), for example. In particular, this may improve the image quality for a transmitted view. The illumination unit may also be a "two-dimensional" illumination and fastened close to the optical opening (for example on the laser pivot arm or on the examination pivot arm); this may improve the image quality in plan view. This may also be an illumination source which is placed close to a recording unit in order to impinge the eye (and the surrounding part of the head) with illumination light from there. This may also be a dark-field illumination. By way of example, the illumination light may be visible light (VIS) or infrared light (IR).

According to a further configuration of the positioning device, the control unit comprises a computing unit designed to carry out any one of the following calculations using the recording data: facial recognition of the patient, recognition of a patient's right or left eye, detection of movements of the patient, reading of a barcode.

To carry out the aforementioned calculations the computing unit comprises an appropriate program which analyzes the recording data and provides the results.

For example, the identity of the patient can be checked by facial recognition. This can avoid errors as a result of incorrect patient data.

Recognition of a patient's right or left eye ensures that the optical opening is positioned in front of the eye intended to be subjected to the therapy. In this case, a large image field size is particularly advantageous since recording data (for example in "plan view") which contain the nose of the patient make it easy to distinguish between the eyes. This also serves to avoid errors.

A warning may be output if an error is identified.

Using the recording data—for example from the side view and/or the plan view—to read a barcode or another code for example allows the recognition of a serial number on a contact element (or associated packaging, for example a data matrix code). This also serves to improve the quality of a laser therapy by avoiding errors. In turn, the large depth of field of the recording optical unit of the recording unit, a large image field size and/or a digital zoom, which is only rendered possible by a large number of pixels of the sensor, are advantageous here.

In addition to the calculations which may for example be performed before the eye is positioned, it is also possible to monitor patient movements during the laser therapy. In this way it is possible to generate a warning signal, a termination signal or an initiation of a termination of the therapy if necessary. Additionally, the well-being of the patient can be detected (especially) during the laser therapy which requires their collaboration and cooperation (e.g., gazing at a fixation light).

For example, recording data of a plan view and/or a side view are used for the aforementioned calculations. To this end, the corresponding recording units for example have a large image field size in their focal planes. Since solutions according to the prior art merely provide recording data in transmitted view only on the patient's eye itself, that is to say with a small image field size, the solution according to the invention can generate particular added value in this context.

The positioning device may comprise more than one display unit. By way of example, a further display unit may be placed away from the location adopted by the operator during the positioning and/or the therapy, said further display unit showing display data to an assistant so that they can also monitor/observe the positioning (and the therapy).

Furthermore, the positioning device may comprise a display unit with a loudspeaker. In addition to the recording data to be displayed visually, the display data may also include acoustic data (audio signals). The acoustic data can relate to notifications or alerts. Such audio data may be generated in the computing unit.

The control unit of the positioning device for example comprises an interface to the recording units, the display unit, the input unit, the displacement unit and/or the illumination unit. Data exchange between the units of the positioning device may be facilitated via this interface (which may also have partial interfaces for communication with only one or a few of these units). Furthermore, the control unit may have an interface to the ophthalmological laser therapy system. Information may be exchanged via this interface, for example patient and treatment data (or alerts, state notifications). These information items may be added to the display data—for example in the computing unit.

According to a for example configuration of the positioning device, the control unit comprises a data interface. Furthermore, the control unit is designed to create a data stream and to provide said data stream via the data interface. Here, the data stream comprises the recording data and/or the display data. The interface may be connected to a storage unit which may be part of the positioning device. Additionally or as an alternative, the interface may be connected to the ophthalmological laser therapy system so that the data stream may be processed further or stored in a storage unit there.

For example, the data stream comprises further data such as control commands, input data, information items from the illumination unit or from the ophthalmological laser therapy system (for example parameters of a therapy laser or patient data), displacement data and/or further calculations from the recording data. If the laser therapy system or the positioning device comprise a microphone for recording microphone data (for example conversations before or during the therapy), these may likewise be part of the data stream.

By way of the data stream (and for example by the storage thereof), the operator is put in a position to document the therapy. Hence, the (stored) data stream may serve as a record of the intervention. Here, the data stream for example comprises not only the preparations of the therapeutic intervention (such as the positioning of the eye or the docking on the contact glass) but also the entire performance thereof. To this end, the data in the data stream may comprise timestamps.

A second aspect of the invention relates to an ophthalmological laser therapy system with an optical opening. According to the invention, the laser therapy system comprises a positioning device in accordance with any one of the above-described explanations.

A third aspect relates to a method for a positioning device of an ophthalmological laser therapy system with an optical opening, for positioning a patient's eye vis-à-vis the optical opening. The positioning device comprises a first recording unit designed to provide first recording data of the eye from a first recording direction and a second recording unit designed to provide second recording data of the eye from a second recording direction. In this case, the second recording direction differs from the first recording direction. Furthermore, the positioning device comprises a displacement unit designed to displace the relative position of the eye vis-à-vis the optical opening on the basis of control commands, and a control unit. The method according to the invention includes the following steps:
  receiving first and second recording data,
  combining the recording data by calculation to form control commands and
  transmitting the control commands to the displacement unit.

An alternative method for a positioning device of an ophthalmological laser therapy system with an optical opening serves the positioning of a patient's eye vis-à-vis the optical opening. The positioning device comprises a first recording unit designed to provide first recording data of the eye from a first recording direction and a second recording unit designed to provide second recording data of the eye from a second recording direction. In this case, the second recording direction differs from the first recording direction. The positioning device furthermore comprises a display unit for displaying the first and second recording data of the eye and a displacement unit designed to displace the relative position of the eye vis-à-vis the optical opening on the basis of control commands. Moreover, the positioning device comprises an input unit designed to facilitate an input of input data, and a control unit. The method according to the invention comprises the following steps:
  receiving first and second recording data,
  displaying the recording data on the display unit,
  receiving input data,
  combining the input data by calculation to form control commands, and
  transmitting the control commands to the displacement unit.

Attention should be drawn to the fact that the described methods are carried out before the actual therapy of the eye; they only serve the preparation of the therapy and are therefore not a part thereof.

It is understood that the features mentioned above and the features still to be explained below can be used not only in the specified combinations but also in other combinations or on their own without departing from the scope of the present invention.

The invention is explained in greater detail below for example with reference to the accompanying drawings, which also disclose features essential to the invention. In detail:

FIG. 1 shows a schematic illustration of an exemplary ophthalmological laser therapy system 50.

The example of the ophthalmological laser therapy system 50 is composed of an appliance base 2 and an appliance head 1 that is adjustable on this appliance base 2 in terms of its height above a ground plane, that is to say the z-direction, and in terms of its position in the plane, that is to say in the x- and y-directions. The appliance head 1 contains a first part of the laser optical unit required for performing the laser therapy. In the example shown, the appliance head 1 also contains the laser source, in this case a femtosecond laser source, required to produce a corresponding pulsed laser beam.

Figure 1:
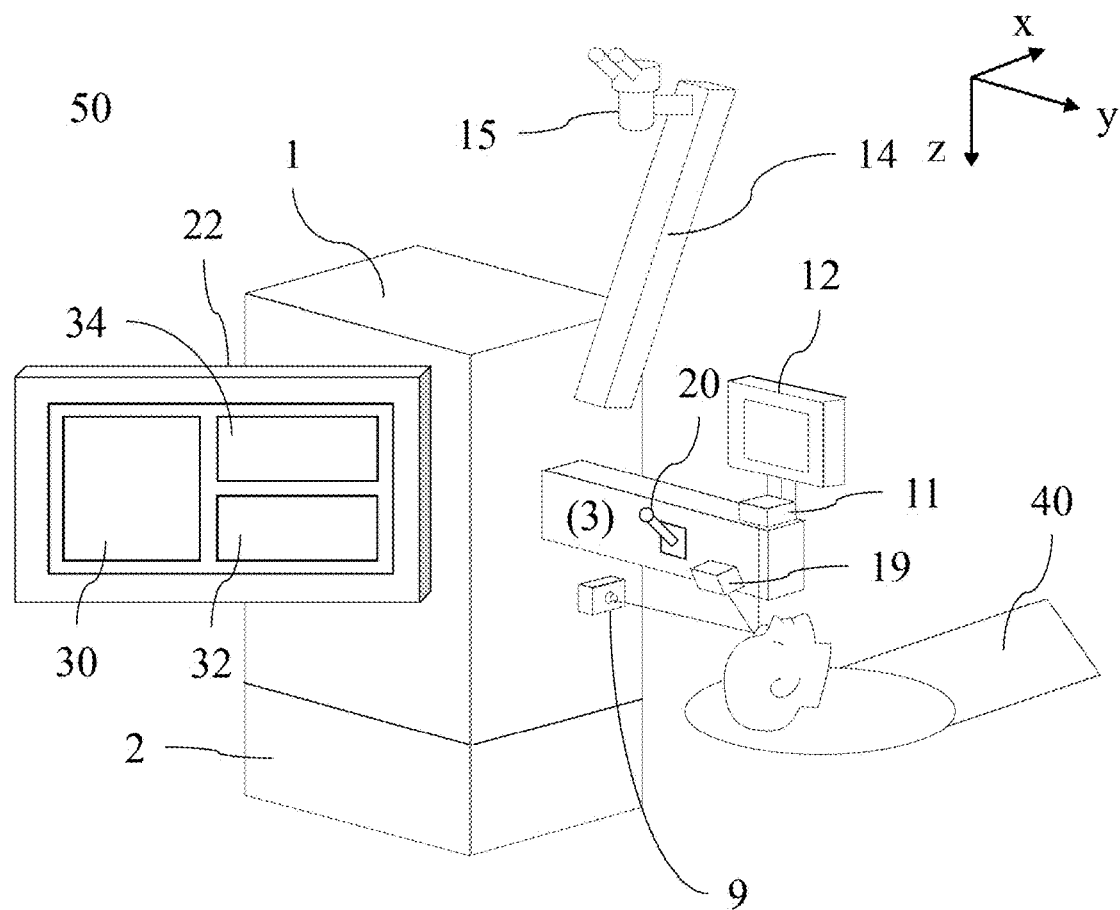
FIG. 1 shows a schematic illustration of an exemplary ophthalmological laser therapy system with a positioning device.

The second part of the laser optical unit is situated in a laser pivot arm 3. The latter can be pivoted about a horizontal axis (not shown) from a rest position, in which it projects upward in approximately perpendicular fashion, to a work position, in which it is arranged approximately horizontally on the appliance head 1, that is to say approximately parallel to the ground plane, and back again. Thus, for laser therapy on the patient's eye, the laser pivot arm 3 can be pivoted over the patient. However, in steps in which the laser pivot arm 3 is not required, it can be brought back into a rest position so that the space above the work position can be used for different things. An optical opening, specifically the laser exit opening from where a therapy laser beam is guided to the therapy location in the patient's eye (when the laser pivot arm 3—as illustrated in FIG. 1—is in the work position), is located on the laser pivot arm 3. The laser exit opening is movably arranged within the laser pivot arm 3.

A first recording unit of the positioning device is designed as a camera 11 which is situated on the laser pivot arm 3. It comprises an optical beam path to the patient's eye which, in sections, is identical to the beam path for the therapy radiation. That is to say, a portion of the laser optical unit in the laser pivot arm 3 is identical to a portion of the optical unit of the recording optical unit of camera 11. The contact glass (not plotted here) is part of this jointly used optical unit. The camera 11 allows recording data of the patient's eye to be recorded in a "transmitted view". The positioning device comprises further cameras 9, 19 (second and third recording unit). These are designed to generate recording data of the patient, that is to say of the patient's eye and of parts of the head surrounding the eye, from recording directions that deviate from the recording direction of camera 11. Additionally, the recording directions of cameras 9 and 19 also differ. Camera 9 facilitates a "side view" of the patient's eye; the recording directions between cameras 11 and 9 include an angle of approximately 90° with respect to one another (vis-à-vis the target position of the eye). Camera 19 facilitates a "plan view" of the patient and the patient's eye. The angle between the recording directions of the second recording unit (camera 9) and the third recording unit (camera 19) is likewise approximately 90°. The angle between the recording directions of the first recording unit (camera 11) and the third recording unit (camera 19) is approximately 55°. The cameras 11, 9 and 19 span a coordinate system with which the head and the patient's eye can be detected in three dimensions. The three-dimensional position of the eye can already be captured by way of camera 11 and camera 9 on account of the arrangements of these two cameras; the determination of the position of the eye will be more accurate or more intuitive for a user wishing to undertake a manual positioning when the recording data of camera 19 are used.

The displacement unit (in this case a part of the patient couch 40) is designed to control a displacement of the appliance head 1 vis-à-vis the appliance base 2. Furthermore, it allows a displacement of the laser exit opening on the laser pivot arm 3. In this way, the laser exit opening can be displaced vis-à-vis the patient's eye in all three spatial dimensions.

The input unit 20 is designed as a joystick. It is located on the laser pivot arm 3. The operator can generate input data by way of the joystick (by moving the joystick or triggering switches or controllers located thereon). The input data are transmitted to a control unit (not illustrated) and are converted into control commands thereby (in a computing unit, likewise not illustrated). In turn, the control commands are transmitted to the displacement unit. In this example, the control unit (with computing unit) is situated in the appliance head 1.

The display unit of the positioning device is designed as a monitor 12 and is likewise fastened to the laser pivot arm 3. It is connected to the laser pivot arm 3 via a rotational pivot (not plotted) in order to ensure a horizontal alignment of the monitor 12 both in the rest position and in the work position. The monitor 12 is designed as a touch screen; consequently, the input unit 20 could also be integrated in the display unit.

Additionally, the positioning device comprises a further display unit 22 which is fastened laterally to the appliance head 1. While the monitor 12 is in a position that is ergonomic for the surgeon (operator), the monitor 22 is placed such that it provides a good view for further observers of the therapy.

The display units 12, 22 show the recording data of the cameras 11, 9 and 19 for the transmitted view 30, the side view 32 and the plan view 34 of the patient's eye.

Furthermore, the laser therapy system 50 comprises an independent examination pivot arm 14, which may be moved about a pivot axis (not plotted). The examination pivot arm 14 can likewise be pivoted back and forth between a rest position and a work position. A surgical microscope 15 is connected to the examination pivot arm 14 about a rotatable axis (not plotted). The pivot axis and the rotatable axis are configured such that the work location of the surgical microscope 15 in the work position coincides with the therapy location. As an alternative or in addition to placement of the first recording unit 11 on the laser pivot arm 3, it is possible to fasten a recording unit to the examination pivot arm 14. By way of example, it may be designed such that it has an optical beam path to the patient's eye which, in sections, is identical to the beam path for examination radiation. That is to say, a portion of the examination optical unit in the examination pivot arm 14 is identical to a portion of the optical unit of the recording optical unit of the camera.

Following the change from the laser pivot arm 3 above the patient's eye to the examination pivot arm 14 above the patient's eye (examination pivot arm 14 is in the work position; laser pivot arm 3 is in the rest position), the recording data of this camera may likewise be displayed on the display unit 12, 22 and/or may be stored in a storage unit for documentation purposes. The stored data of the documentation may also include audio signals, microphone data or patient and treatment data. The recording data displayed on the display units 12, 22 may be chosen according to which pivot arm is in its work position. For example, only the recording data of the recording unit linked to the respective pivot arm currently in its work position are shown in transmitted view.

Attention should be drawn to the fact that the positioning device according to the invention is not restricted to use in an ophthalmological laser therapy system 50 with a laser pivot arm 3 and an examination pivot arm 14. Rather use is likewise possible and advantageous in a laser therapy system 50 which comprises a laser pivot arm 3 that may be positioned but cannot be brought into a rest position and/or which does not comprise an examination pivot arm 14.

Figure 2:
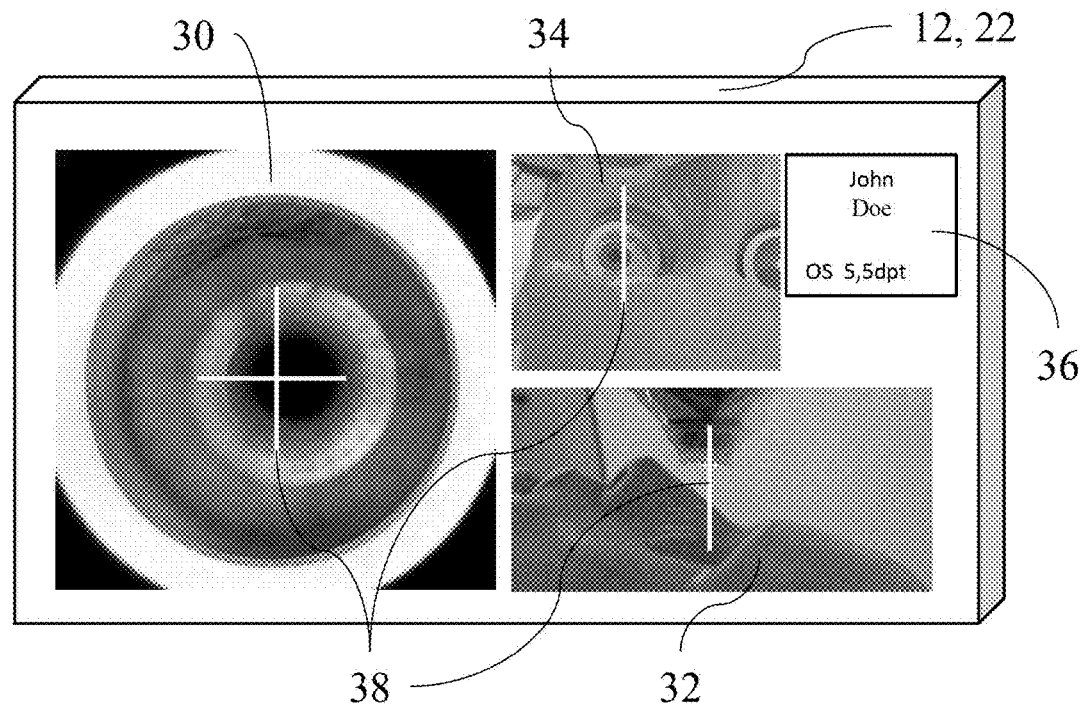
FIG. 2 shows a schematic illustration of the presentation of recording data on a display unit.

FIG. 2 shows a schematic illustration of the presentation of recording data on a display unit 12, 22. According to the invention, the display units 12 and 22 are used to display a plan view 34, obtained with camera 19, a side view 32, generated by camera 9, and also the transmitted view 30, observed through the contact glass onto the patient's eye and generated by camera 11, to the operator while positioning the patient's eye vis-à-vis the optical opening (e.g., the laser exit opening and/or contact glass). Camera 19 and the display of its image 34 on the monitor 12 increase the ergonomics for the surgeon since the patient is partly covered during surgery by the laser pivot arm 3 which contains the laser optical unit. For example, the recording data (for example in the plan view) are also displayed following the positioning of the eye, for example for monitoring the therapy.

Target marks 38 are overlaid on the displayed recording data. The positioning of the eye vis-à-vis the optical opening can be improved with the aid of the target marks 38. In particular, the direction in which the joystick 20 needs to be moved/controlled so that the patient's eye reaches its target position is quickly and intuitively evident to the operator.

Additionally, information data 36 are displayed on the display unit 12, 22. These are provided to the control unit by the laser therapy system via an interface. Furthermore, it is possible to output alerts which are provided by the laser therapy system or the control unit (or the computing unit).

Figures 3A, 3B, 3C:
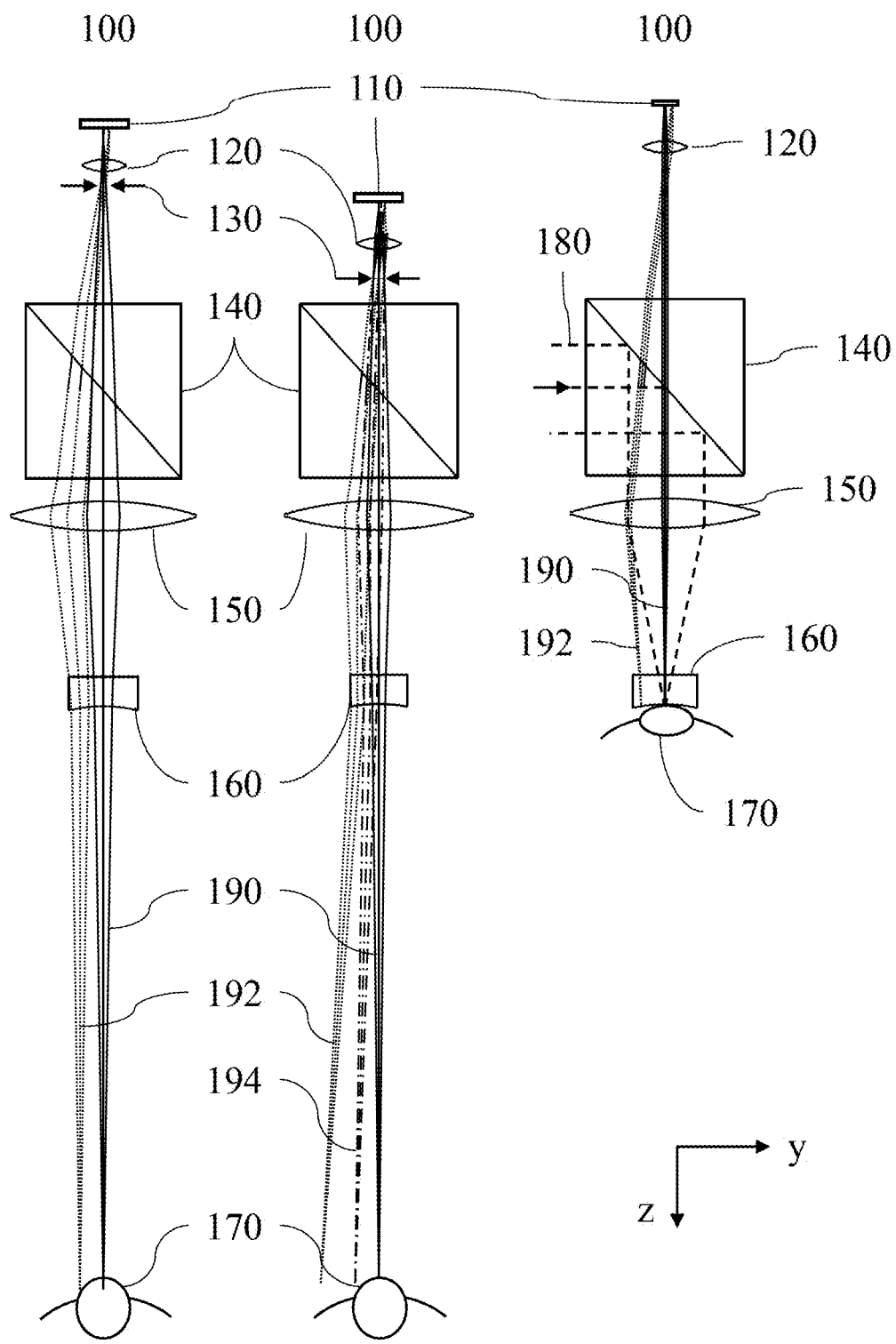
FIG. 3a, 3b, 3c show sectional images of an exemplary embodiment of the recording optical unit of a recording unit.

Sectional images of the recording optical unit of a recording unit 100 are displayed in FIGS. 3a, 3b and 3c. Here, this is a recording unit 100 having a recording optical unit which is partly identical to the laser optical unit of the ophthalmological laser therapy system. An eye 170, an objective lens 150 with a contact element 160 for the laser treatment, a beam splitter 140 and a camera objective lens 120 with a stop 130, and a sensor 110 (CCD or CMOS detector) are illustrated. Here, the contact element 160, the objective lens 150 and the beam splitter 140 are jointly used by the laser optical unit and the recording optical unit. The optical design of the recording optical unit is distinguished in that it has a small numerical aperture in order thus to ensure a large depth of field. In this way, the eye 170 is already imaged so sharply at a distance of 100 mm to 200 mm from the contact element 160 that a centration of the eye 170 is facilitated. The imaging scale and the free diameters of the optical elements are chosen such that an image field with a diameter of approximately 10 mm is imaged in focus at the contact element 160, which is the target position of the eye.

In FIG. 3*a*, the course of the beam from the sensor 110 to the contact element 160 is formed such that the area with a diameter of 10 mm is imaged with the same size, also for distances from 100 mm to 250 mm. To this end, the stop 130 is positioned such that object-side telecentricity is ensured. This is elucidated by the beam 190 (solid line) for the center of the area to be imaged and by the beam 192 (dotted line) for a marginal region of the area to be imaged. In FIG. 3*a*, the beams 190 and 192 run in parallel and do not change their spacing.

FIG. 3*b* illustrates an example variant in this respect. Here, the optical design is designed such that the image field of the imaged area increases in the case of a greater distance from the contact element 160, and so a larger part of the eye or of the patient's head is imaged on the camera sensor 110. This facilitates an improved "capture" of the eye at the start of a positioning, when eye 170 and contact element 160 are still at a large distance from one another. This is elucidated by the beam 190 (solid line) for the center of the area to be imaged, by the beam 192 (dotted line) for a marginal region and by the beam 194 (dash-dotted line) for a central region of the area to be imaged. The distance between the beams 190, 192 and 194 increases with the distance from the contact element 160.

The contact element 160 may be formed as a plane or curved (as shown here) contact glass. The telecentricity (or deviation therefrom) is determined by the distance between the objective lens 150 and camera objective lens 120 or the stop 130 thereof.

The beam paths of the recording unit and the laser optical unit are combined in the beam splitter 140. The latter is designed as a beam splitter cube in FIGS. 3*a*, 3*b* and 3*c*. However, an embodiment as a splitter plate is also possible.

For elucidation purposes, the course of the beam of therapy radiation 180 is plotted as a dashed line for the jointly used optical unit in FIG. 3*c*. In this case, the eye 170 is in its target position; it is in contact with the contact element 160.

Figure 4:
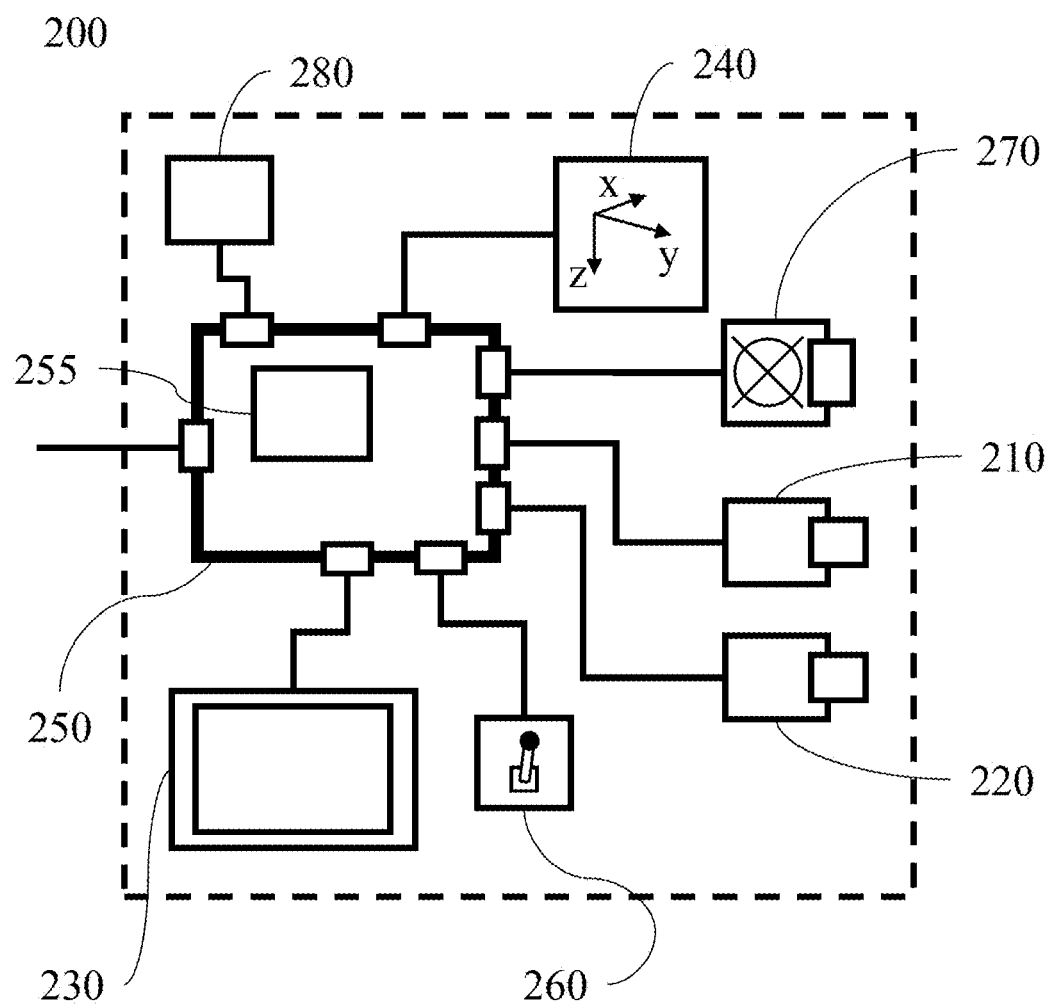
FIG. 4 shows a schematic illustration of an exemplary embodiment of a positioning device.

FIG. 4 illustrates a schematic illustration of an exemplary embodiment of a positioning device 200. The positioning device 200 comprises a first recording unit 210, a second recording unit 220, a display unit 230 and a displacement unit 240. Furthermore, the exemplary embodiment of the positioning device 200 comprises an input unit 260, an illumination unit 270 and a storage unit 280. A data exchange from the units to the control unit 250 is realized by way of interfaces (illustrated as boxes on the control unit). In this case, the data exchange is implemented by way of cables; it can also be implemented wirelessly. Furthermore, an interface is configured for an exchange of data with the laser therapy system 50 (illustrated by way of a line which leaves the positioning device 200 illustrated by a dashed line). The control unit 250 comprises a computing unit 255 which allows the calculation of displacement data.

In this case, the aforementioned features of the invention, which are described in various exemplary embodiments, can be used not only in the specified exemplary combinations but also in other combinations or on their own, without departing from the scope of the present invention.

A description of an apparatus relating to method features is analogously applicable to the corresponding method with respect to these features, while method features correspondingly represent functional features of the apparatus described.

The invention claimed is:

1. A positioning device for an ophthalmological laser therapy system with an optical opening, for positioning a patient's eye vis-à-vis the optical opening, the positioning device comprising:
   a first recording unit configured to provide first recording data of the eye from a first recording direction,
   a second recording unit configured to provide second recording data of the eye from a second recording direction,
   the second recording direction differing from the first recording direction,
   a third recording unit configured to provide third recording data of the eye from a third recording direction, the third recording direction differing from both the first recording direction and the second recording direction, wherein the first recording unit, the second recording unit, and the third recording unit are capable of simultaneously providing the first recording data, the second recording data, and the third recording data, respectively, from the first recording direction, the second recording direction, and the third recording direction;
   a displacement unit configured to displace a relative position of the eye vis-à-vis the optical opening on the basis of control commands, wherein the displacement unit includes at least one of a displaceable appliance head movable relative to an appliance base and a displaceable patient couch moveable relative to the appliance base, whereby the optical opening is displaceable relative to the patient's eye in three spatial dimensions, and
   one of
      a first controller configured to receive the first recording data, the second recording data and the third recording data and to generate the control commands on the basis of the first recording data, the second recording data and the third recording data and to communicate the control commands to the displacement unit;
   or
      an input interface configured to facilitate an input of input data, and
      a second controller configured to generate control commands on the basis of the first recording data, the second recording data and the third recording data, on the basis of the input data or both and to provide the control commands to the displacement unit.

2. The positioning device according to claim 1, wherein the first recording unit comprises a first recording optical unit and the second recording unit comprises a second recording optical unit, at least one of the first recording optical unit and the second recording optical unit having on an object side a numerical aperture selected from a group consisting of less than 0.25, less than 0.1, and less than 0.05.

3. The positioning device according to claim 2, wherein the first recording optical unit is configured such that an image field of an observed area is imaged with a constant image field size or a larger image field size with increasing distance from the first recording optical unit.

4. The positioning device according to claim 1, wherein the ophthalmological laser therapy system further comprises an optical unit, wherein the first recording unit comprises a first recording optical unit, a part of the optical unit of the ophthalmological laser therapy system and a part of the first recording optical unit being identical.

5. The positioning device according to claim 4, wherein the first recording optical unit is configured such that an image field of an observed area is imaged with a constant image field size or a larger image field size with increasing distance from the first recording optical unit.

6. The positioning device according to claim 1, wherein a recording unit has an image field size selected from a group consisting of at least 30 mm×30 mm, at least 40 mm×40 mm, and at least 50 mm×50 mm in a focal plane.

7. The positioning device according to claim 1, wherein the first recording direction and the second recording direction include an angle with respect to one another selected from a group consisting of 90°±30°, 90°±10°, and 90°±5°.

8. The positioning device according to claim 1, wherein the third recording direction and the first recording direction include an angle with respect to one another selected from a group consisting of between 100 and 90°, between 20° and 700, and between 300 and 60°.

9. The positioning device according to claim 1, wherein the first controller or the second controller comprises a computing unit configured to combine recording data from a recording unit with a target mark by calculation to form display data, and wherein the first controller or the second controller provides the display data.

10. The positioning device according to claim 1, wherein the positioning device comprises an illumination unit configured to impinge the eye with illumination light.

11. The positioning device according to claim 1, wherein the first controller or the second controller comprises a computing unit designed to carry out at least one of the following calculations using the recording data:
facial recognition of the patient,
recognition of a patient's right or left eye,
reading of a barcode,
detection of movements of the patient.

12. The positioning device according to claim 1, wherein the first controller or the second controller comprises a data interface and wherein the first controller or the second controller is configured to create a data stream which comprises the recording data, the display data or both and to provide the data stream via the data interface.

13. An ophthalmological laser therapy system with an optical opening and comprising a positioning device according to claim 1.

14. A method for a positioning device of an ophthalmological laser therapy system with an optical opening, for positioning a patient's eye vis-à-vis the optical opening, the positioning device comprising:
a first recording unit configured to provide first recording data of the eye from a first recording direction,
a second recording unit configured to provide second recording data of the eye from a second recording direction,
the second recording direction differing from the first recording direction,
a third recording unit configured to provide third recording data of the eye from a third recording direction, the third recording direction differing from both the first recording direction and the second recording direction,
wherein the first recording unit, the second recording unit, and the third recording unit are capable of simultaneously providing the first recording data, the second recording data, and the third recording data, respectively, from the first recording direction, the second recording direction, and the third recording direction,
a displacement unit configured to displace the relative position of the eye vis-à-vis the optical opening on the basis of control commands, wherein the displacement unit includes at least one of a displaceable appliance head movable relative to an appliance base and a displaceable patient couch moveable relative to the appliance base, whereby the optical opening is displaceable relative to the patient's eye in three spatial dimensions, and
a controller,
wherein the method comprises the following steps:
receiving the first recording data, the second recording data, and the third recording data,
combining the first recording data, the second recording data and the third recording data by calculation to form control commands and
transmitting the control commands to the displacement unit.

15. A method for a positioning device of an ophthalmological laser therapy system with an optical opening, for positioning a patient's eye vis-à-vis the optical opening, the positioning device comprising:
a first recording unit configured to provide first recording data of the eye from a first recording direction,
a second recording unit configured to provide second recording data of the eye from a second recording direction,
the second recording direction differing from the first recording direction,
a third recording unit configured to provide third recording data of the eye from a third recording direction, the third recording direction differing from both the first recording direction and the second recording direction,
wherein the first recording unit, the second recording unit, and the third recording unit are capable of simultaneously providing the first recording data, the second recording data, and the third recording data, respectively, from the first recording direction, the second recording direction, and the third recording direction,
a display unit that displays the first recording data, the second recording data and the third recording data of the eye,
a displacement unit configured to displace the relative position of the eye vis-à-vis the optical opening on the basis of control commands, wherein the displacement unit includes at least one of a displaceable appliance head movable relative to an appliance base and a displaceable patient couch moveable relative to the appliance base, whereby the optical opening is displaceable relative to the patient's eye in three spatial dimensions,
an input unit configured to facilitate an input of input data, and
a controller,
wherein the method comprises:
receiving the first recording data, the second recording data and the third recording data,
displaying the first recording data, the second recording data and the third recording data on the display unit,
receiving input data,
combining the input data by calculation to form control commands and
transmitting the control commands to the displacement unit.

* * * * *

UNITED STATES PATENT AND TRADEMARK OFFICE
CERTIFICATE OF CORRECTION

PATENT NO. : 12,324,771 B2  
APPLICATION NO. : 17/637796  
DATED : June 10, 2025  
INVENTOR(S) : Böhme et al.

Page 1 of 1

It is certified that error appears in the above-identified patent and that said Letters Patent is hereby corrected as shown below:

In the Specification

Column 1, Line 8, delete "No. 10 2019 213 98.2" and insert --No. 10 2019 213 698.2--

Column 12, Line 13, delete "FIG." and insert --FIGS.--

In the Claims

Column 17, Line 17, delete "100" and insert --10°--

Column 17, Line 18, delete "700" and insert --70°--

Column 17, Line 18, delete "300" and insert --30°--

Signed and Sealed this  
Second Day of September, 2025

Coke Morgan Stewart  
*Acting Director of the United States Patent and Trademark Office*